(12) United States Patent
Kara et al.

(10) Patent No.: US 10,023,820 B2
(45) Date of Patent: Jul. 17, 2018

(54) DEVICE AND METHOD FOR PRODUCING SUBSTITUTE NATURAL GAS AND NETWORK COMPRISING SAME

(71) Applicant: GDF SUEZ, Courbevoie (FR)

(72) Inventors: Yilmaz Kara, Eaubonne (FR); Bernard Marchand, Paris (FR); Sandra Capela, Pantin (FR)

(73) Assignee: GDF SUEZ, Courbevoie (FR)

( * ) Notice: Subject to any disclaimer, the term of this patent is extended or adjusted under 35 U.S.C. 154(b) by 0 days.

(21) Appl. No.: 15/032,153

(22) PCT Filed: Oct. 28, 2014

(86) PCT No.: PCT/FR2014/052745
§ 371 (c)(1),
(2) Date: Apr. 26, 2016

(87) PCT Pub. No.: WO2015/063411
PCT Pub. Date: May 7, 2015

(65) Prior Publication Data
US 2016/0257897 A1    Sep. 8, 2016

(30) Foreign Application Priority Data
Oct. 28, 2013  (FR) ...................................... 13 60488

(51) Int. Cl.
*C10L 3/08*     (2006.01)
*B01J 8/04*     (2006.01)
(Continued)

(52) U.S. Cl.
CPC . *C10L 3/08* (2013.01); *B01J 8/04* (2013.01); *C07C 1/0485* (2013.01); *C07C 1/12* (2013.01);
(Continued)

(58) Field of Classification Search
None
See application file for complete search history.

(56) References Cited

U.S. PATENT DOCUMENTS 2,474,345 A * 6/1949 Clark ..................... C10G 1/002
                                                     201/28
5,711,770 A * 1/1998 Malina .................... C01B 3/042
                                                     204/194

(Continued)

FOREIGN PATENT DOCUMENTS

EP    2 505 632 A2    10/2012
FR    2 982 857 A1    5/2013
WO    WO 02102943 A1 * 12/2002 ................ C10L 3/08

OTHER PUBLICATIONS

Saric et al., "Power-To-Gas coupling to biomethane production," ICPS 13 International Conference on Polygeneration Strategies, Sep. 1, 2013, Vienna, Austria.

(Continued)

*Primary Examiner* — Jennifer A Leung
(74) *Attorney, Agent, or Firm* — PatShegen IP

(57) ABSTRACT

A device includes a gasifier to produce a gaseous compound from a biomass. The gasifier includes inlets for the biomass and for an oxidizing agent and an outlet for the gaseous compound including carbon monoxide. A first methanation unit to methanate the carbon monoxide to produce a substitute natural gas exiting the gasifier. The first methanation unit includes at least one inlet for water and an inlet for the gaseous compound coming from the gasifier. A second methanation unit to methanate the carbon dioxide to produce the substitute natural gas. The second methanation unit includes at least one inlet for water and one inlet for the carbon dioxide from the first methanation unit. A dihydrogen producing unit to produce dihydrogen from water and electric current. The dihydrogen producing unit includes an
(Continued)

electrical power supply, an inlet for water and an outlet for dihydrogen supplying the second methanation unit.

21 Claims, 3 Drawing Sheets

(51) Int. Cl.
*C10J 3/12* (2006.01)
*C07C 1/04* (2006.01)
*C07C 1/12* (2006.01)
*C10J 3/82* (2006.01)
*C10J 3/84* (2006.01)

(52) U.S. Cl.
CPC . *C10J 3/12* (2013.01); *C10J 3/82* (2013.01); *C10J 3/84* (2013.01); *C10J 2300/0916* (2013.01); *C10J 2300/0976* (2013.01); *C10J 2300/1662* (2013.01); *C10J 2300/1684* (2013.01); *C10J 2300/1807* (2013.01); *C10J 2300/1853* (2013.01); *C10L 2290/02* (2013.01); *C10L 2290/04* (2013.01); *C10L 2290/06* (2013.01); *C10L 2290/10* (2013.01); *C10L 2290/38* (2013.01); *C10L 2290/562* (2013.01); *Y02E 60/366* (2013.01)

(56) References Cited

U.S. PATENT DOCUMENTS

| 2002/0134019 A1* | 9/2002 | Paisley | C10B 49/22 48/197 R |
| 2008/0190024 A1* | 8/2008 | Hobbs | C10G 27/04 48/76 |
| 2012/0091730 A1* | 4/2012 | Stuermer | C25B 1/04 290/1 R |

OTHER PUBLICATIONS

"Research for global markets for renewable energies," Apr. 1, 2011, pp. 69-78, Berlin, https://web.archive.org/web/20110923171659/http://www.fvee.de/fileadmin/publikationen/Themenhefte/th2009-1/th2009-1.pdf.

* cited by examiner

DEVICE AND METHOD FOR PRODUCING SUBSTITUTE NATURAL GAS AND NETWORK COMPRISING SAME

RELATED APPLICATIONS

This application is a § 371 application from PCT/FR2014/052745 filed Oct. 28, 2014, which claims priority from French Patent Application No. 13 60488 filed Oct. 28, 2013, each of which is herein incorporated by reference in its entirety.

TECHNICAL FIELD OF THE INVENTION

The present invention relates to a device and method for producing substitute natural gas and a network comprising same. It applies in particular to industrial methanation and the cogeneration of thermal energy and methane.

STATE OF THE ART

Methanation is an industrial process that catalytically converts hydrogen and carbon monoxide or carbon dioxide into methane.

The formula for the methanation reaction varies according to the nature of the carbon-based compound. Depending on the case, this formula is:

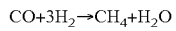

$CO+3H_2 \rightarrow CH_4+H_2O$

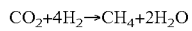

$CO_2+4H_2 \rightarrow CH_4+2H_2O$

Usually, a biomethane production device for which biomass is the main input comprises three main elements. The first element is a means of gasifying the biomass into synthetic gas (also called "syngas"). This syngas is mainly composed of non-condensable gases such as, for example, $H_2$, CO, $CO_2$ or $CH_4$. For certain methods, as well as the syngas produced the gasification means also produces tar-type condensable gases, hereinafter referred to as "tars", and solid residues of "char" type, i.e. a solid portion resulting from pyrolysis of a solid combustible.

The gasification means is associated with a combustion means in which the solid residues, such as the chars, are burnt to maintain the temperature of the gasification means. This combustion means is normally a moving or circulating bed reactor. This fluidized medium is preferably comprised of particles of olivine catalyst, and more preferably of a heat-transfer solid such as sand, for example. This fluidized medium makes it possible to facilitate the extraction of residual chars that have not reacted in the gasification means and to facilitate the transporting of these chars to the combustion means.

The second main element is the catalytic methanation of the gasified biomass, this methanation consisting of converting the $H_2$ and CO into $CH_4$ (SNG, for "Synthetic Natural Gas").

The third main element is bringing the residual SNG up to specification, i.e. eliminating the residual $H_2$, CO, $H_2O$ and $CO_2$ so as to produce an SNG as close as possible to the specifications for injection into the natural gas grid, in particular in terms of higher heating value, referred to as "HHV", and the Wobbe index. As a reminder, the Wobbe index makes it possible to evaluate the capacity for interchangeability between gases, fuels or combustibles.

The main drawback of the current systems stems from the absence of optimization in the SNG yield on output from the system due to numerous carbon and energy losses throughout the chain described above.

OBJECT OF THE INVENTION

The present invention aims to remedy all or part of these drawbacks.

To this end, the present invention envisages, according to a first aspect, an integrated device for producing substitute natural gas that comprises:
  a gasifier configured for producing a gaseous compound from a biomass, comprising:
    an inlet for the biomass;
    an inlet for an oxidizing agent; and
    an outlet for the gaseous compound comprising carbon monoxide;
  a means for methanating the carbon monoxide to produce substitute natural gas from the gaseous compound output from the gasifier, the carbon monoxide methanation means comprising at least one inlet for water and an inlet for the gaseous compound coming from the gasifier;
  a means for methanating carbon dioxide to produce substitute natural gas comprising at least one inlet for water and an inlet for the carbon dioxide coming from the carbon monoxide methanation means;
  a means for producing dihydrogen from water and electric current comprising:
    an electrical power supply;
    an inlet for water and
    a dihydrogen outlet supplying the carbon dioxide methanation means.

It is noted that a "gasifier" is, by misuse of the language, sometimes called a "gasificator".

Thanks to these provisions, the carbon dioxide present on output from the carbon monoxide methanation means is transformed into SNG by the carbon dioxide methanation means, thus increasing the carbon conversion yield of the device as a whole. In addition, the presence of a means of electrolyzing water allows "power to gas" types of applications to be realized. As a reminder, power-to-gas applications consist of converting unused electrical energy, for example produced at night by a nuclear power station, into substitute gas that can be used subsequently to regenerate electrical energy.

In some embodiments, the device that is the subject of the present invention also comprises a combustion means comprising:
  an inlet for a solid portion resulting from pyrolysis of a non-gasified solid combustible, also called "char", coming from the gasifier and transported by a heat transfer medium;
  an oxidizer inlet;
  a non-gasified char combustion means for heating the heat transfer medium;
  a heat transfer medium outlet linked to a heat transfer medium inlet of the gasifier; and
  an outlet for flue-gases.

The advantage of these embodiments is that they allow the gasifiers yield to be increased by using non-gasified carbonized residuals to generate heat heating the gasifier. The combustion of these carbonized residuals also allows the heat-transfer medium transporting the carbonized residuals to be heated.

In some embodiments, the dihydrogen production means is configured to carry out an electrolysis of water, comprising a dioxygen outlet supplying the oxidizer inlet of the combustion means.

These embodiments have the advantage of dramatically increasing the yield of substitute natural gas by making it possible to avoid injecting a portion of the synthetic gas coming from the gasifier into the combustion means so as to make combustion possible. In particular, these embodiments allow a power-to-gas application's efficiency to be maximized by using all of the products from the electrolysis of water and by optimizing the yield of substitute natural gas.

In some embodiments, the device that is the subject of the present invention comprises, between the gaseous compound outlet of the gasifier and the gaseous compound inlet of the carbon monoxide methanation means, a separator configured to separate the gases from the solids and/or tars in the gaseous compound and to transmit the separated solids and/or tars to the combustion means.

The first advantage of these embodiments is that they allow the synthetic gas coming from the gasifier to be purified by removing solids that might be transported with the gas. The second advantage of these embodiments is that they allow the solids to be recycled by using them in the combustion means, thus increasing the yield of the combustion means.

In some embodiments, the device that is the subject of the present invention comprises a means of recycling a portion of the flue-gas, on output from the combustion means, comprising dioxygen, towards an oxidizer inlet of the combustion means.

These embodiments allow the yield of the combustion means to be increased by recycling a portion of the products from the combustion means. These embodiments make it possible for a given piece of equipment to be able to operate equally well with air-combustion as with oxy-combustion. For a method initially designed to operate using air-combustion, the fact of switching to oxy-combustion results in a drastic fall in speeds and leads to the stopping of the circulation of the heat-transfer solid, and therefore of the production of gas. In this case, in order to switch to oxy-combustion either a new combustion means with a smaller diameter, to have suitable transport speeds, or a recirculation of flue-gas, to compensate for the absence of nitrous oxide in the oxidizer, is necessary. The choice of flue-gases is certainly the most relevant since this is a product coming from the same system.

In some embodiments, the device that is the subject of the present invention comprises, downstream from the flue-gas outlet of the combustion means, a carbon dioxide separator configured to supply the carbon dioxide methanation means with carbon dioxide.

These embodiments allow the yield of the carbon dioxide methanation means to be increased.

In some embodiments, the device that is the subject of the present invention comprises a dihydrogen separator downstream from the carbon monoxide methanation means in order to supply said carbon monoxide methanation means with dihydrogen.

These embodiments allow the yield of the carbon monoxide methanation means to be increased. These embodiments are preferred in the case where the Wobbe index or the higher heating value of the synthetic gas does not comply with the requirements of the gas transmission network to which the synthetic gas is supplied.

In some embodiments, the device that is the subject of the present invention comprises downstream from the carbon monoxide methanation means, a carbon dioxide separator for supplying the carbon dioxide methanation means.

These embodiments make it possible to separate the methane on output from the carbon monoxide methanation means from the carbon dioxide to be supplied to the carbon dioxide methanation means. In this way, the gas has a higher concentration of carbon dioxide on input to the carbon dioxide methanation means, as a result increasing the yield on output from the carbon dioxide methanation means.

In some embodiments, an outlet from the carbon dioxide methanation means is linked to an outlet from the carbon monoxide methanation means.

These embodiments make it possible to minimize the number of devices required between the outlets from each methanation means and a substitute natural gas outlet of the device.

In some embodiments, the device that is the subject of the present invention comprises, downstream from the carbon monoxide methanation means and/or from the combustion means, a condenser configured to condense the water contained in vapors and to supply the electrolysis means with water.

These embodiments allow the yields of the electrolysis means to be increased.

According to a second aspect, the present invention envisages a network, which comprises at least one device that is the subject of the present invention.

As the particular features, advantages and aims of the network are identical to those of the device that is the subject of the present invention, they are not repeated here.

In some embodiments, the network that is the subject of the present invention so also comprises a multi-energy management means for controlling:
the production, with at least one device that is the subject of the present invention, and storage of methane during periods of surplus electricity production; and
the production of electricity with the stored methane outside these periods.

These embodiments allow the amount of energy available in the network to be optimized during the periods when the electricity produced is not in surplus.

In some embodiments, the network that is the subject of the present invention comprises gas distribution pipelines, the storage of methane for generating electricity being realized by overpressure above the nominal pressure of the pipelines.

These embodiments allow the methane produced by the device that is the subject of the present invention to be stored at lower cost.

According to a third aspect, the present invention envisages a method for producing substitute natural gas that comprises:
a gasification step for producing a gaseous compound from a biomass, comprising:
a step of inputting the biomass;
a step of inputting an oxidizing agent; and
a step of outputting the gaseous compound comprising carbon monoxide;
a step of methanating the carbon monoxide to produce substitute natural gas from the gaseous compound output from the gasification step, the carbon monoxide methanation step comprising at least one input step for water and for the gaseous compound from the gasifier;
a step of methanating carbon dioxide to produce substitute natural gas comprising at least one input step for water and an input for carbon dioxide coming from the carbon monoxide methanation step;
a step of producing dihydrogen from water and electric current comprising:
a step of supplying electrical power;
a water input step and
an output step for dihydrogen used during the carbon dioxide methanation step.

As the particular features, advantages and aims of the network are identical to those of the device that is the subject of the present invention, they are not repeated here.

BRIEF DESCRIPTION OF THE FIGURES

Other particular advantages, aims and features of the invention will become apparent from the non-limiting description that follows of at least one particular embodiment of the device and method for producing substitute natural gas and of the network comprising said device that are the subjects of the present invention, with reference to drawings included in an appendix, wherein.

DESCRIPTION OF EXAMPLES OF REALIZATION OF THE INVENTION

The present description is given as a non-limiting example.

It is now noted that the figures are not to scale.

Figure 1:
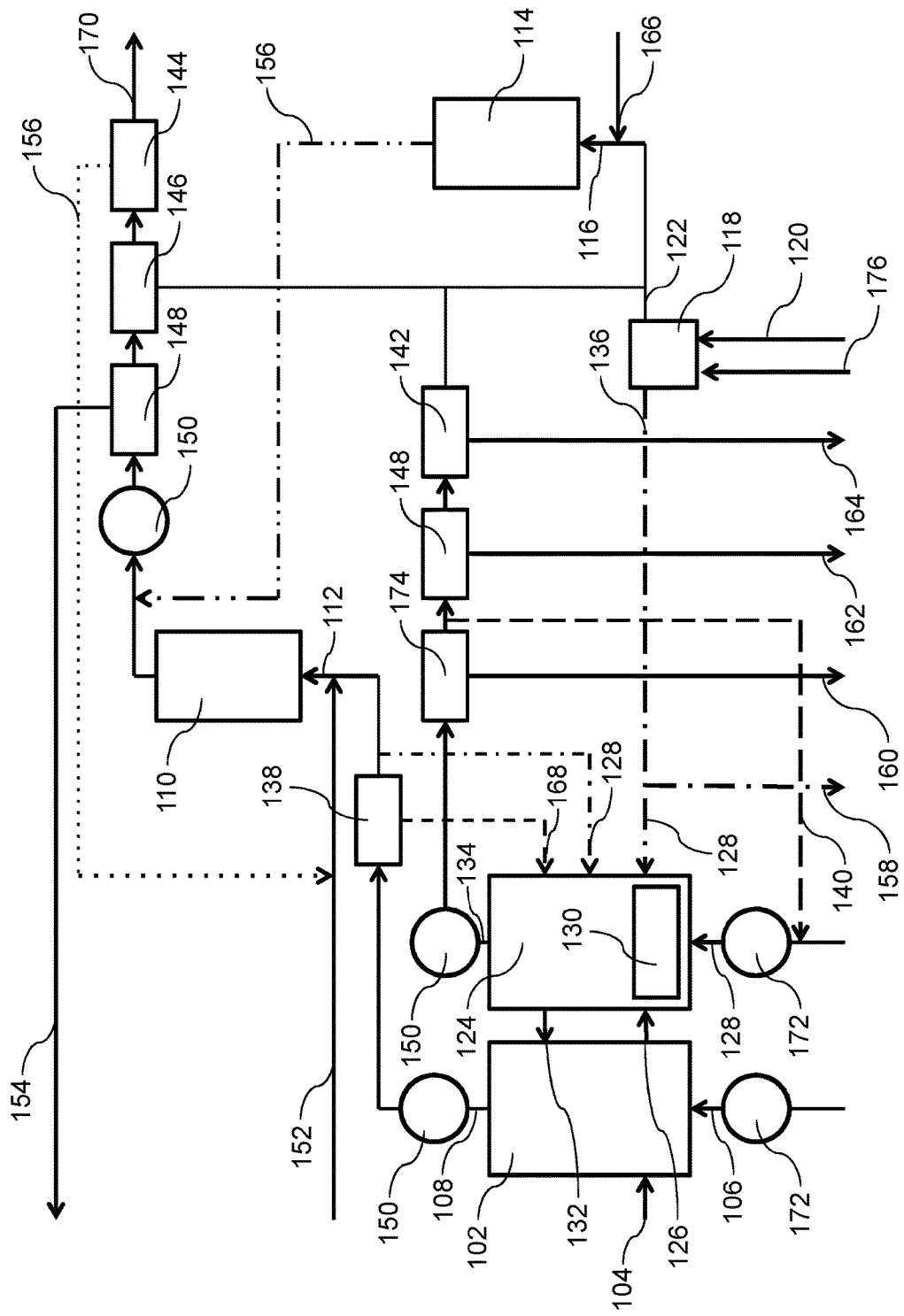
FIG. 1 represents, schematically, a particular embodiment of the device for producing substitute natural gas that is the subject of the present invention.

FIG. 1 shows an embodiment of the integrated device for producing substitute natural gas that is the subject of the present invention. This device comprises:
- a gasifier 102, comprising:
  - an inlet 104 for biomass;
  - an inlet 106 for an oxidizing agent; and
  - an outlet 108 for synthetic gas comprising carbon monoxide;
- a separator 138 configured to transmit separated solids and tars to the combustion means 124;
- a means 110 of methanating the carbon monoxide output from the gasifier 102, comprising at least one inlet 112 for water and for synthetic gas coming from the gasifier 102, supplying methane and carbon dioxide;
- a dihydrogen separator 144;
- a first carbon dioxide separator 146;
- a carbon dioxide methanation means 114, comprising at least one inlet 116 for water and for carbon dioxide coming from the carbon monoxide methanation means, supplying methane;
- a means 118 of electrolyzing water comprising:
  - an electric power supply 176;
  - a water inlet 120;
  - a dioxygen outlet 136; and
  - a dihydrogen outlet 122; and
- a combustion means 124, comprising:
  - an inlet 126 for non-gasified char transported by a heat transfer medium coming from the gasifier 102;
  - three inlets 128;
  - a combustion means 130 for the non-gasified char, tars and make-up syngas for heating the heat transfer medium;
  - a heat transfer medium outlet 132 linked to a heat transfer medium inlet of the gasifier 102 and
  - an outlet 134 for flue-gases;
  - an inlet 168 for non-gasified char and for tars separated from the gas coming from the gasifier 102; and
  - a means 140 of recycling a portion of the flue-gas coming from the combustion means 124;
- a second carbon dioxide separator 142; and
- two condensers 148;
- three cooling means 150;
- two heating means 172;
- a first water vapor inlet 152;
- a dioxygen outlet 158;
- an ash and solid residues outlet 160;
- a first water outlet 154;
- a second water outlet 162;
- an outlet 164 for gas not used by the device;
- a second water vapor inlet 166; and
- a substitute natural gas outlet 170.

The gasifier 102 is, for example, a reactor in which the supplied biomass undergoes a thermochemical conversion to form a synthetic gas (also called "syngas") containing dihydrogen, carbon monoxide, carbon dioxide, water, tars, or, in general, any type of carbonized compound. This gasifier 102 comprises a biomass inlet 104 that is, for example, a valve, a dispensing screw or a hopper allowing the biomass to be introduced into the reactor. This gasifier 102 also comprises an oxidizing agent inlet 106 that is, for example, a valve allowing water vapor to be introduced into the reactor. Upstream from this oxidizing agent inlet 106, a heating means 172 is positioned such that the incoming oxidant does not disturb the thermal balance inside the gasifier 102.

The gasifier 102 also comprises a non-gasified char outlet (not shown) that is, for example, a pipe into which a fluidized heat-transfer medium is transferred. This fluidized heat-transfer medium consists, for example, of olivine or sand, and supplies the necessary energy to the thermochemical conversion of the biomass. This gasifier 102 also comprises a fluidized heat-transfer medium inlet, not shown. Lastly, this gasifier 102 comprises a synthetic gas outlet 108 that is, for example, a pipe connected to the reactor.

In order to heat the gasifier 102, the device comprises a combustion means 124. This combustion means 124 is, for example, a reactor. This combustion means 124 comprises an inlet 126 for non-gasified char transported by a heat-transfer medium from the gasifier 102 that is, for example, a pipe linking the gasifier 102 to the combustion means 124. This combustion means 124 also comprises three oxidizer inlets 128 that are, for example, valves linked to pipes allowing the oxidizer to be introduced into the combustion means 124. One inlet 128 is configured to insert air, nitrogen or dioxygen, or a mixture of all of these, for example air enriched with dioxygen, into the combustion means 124. Upstream from this inlet 128, an, optional, means 172 of heating the oxidizer is placed such that the oxidizer input does not disturb the internal thermal balance of the combustion means 124. Another inlet 128 is configured to insert dioxygen coming from the electrolysis of water into the combustion means 124. The last inlet 128 is configured to insert, if necessary, synthetic gas coming from the gasifier 102 into the combustion means 124, as a thermal booster in the case where char and tars are not sufficient.

In some variants, these oxidizer inlets 128 can be combined into two or just one oxidizer inlet. The combustion means 124 performs the combustion of the non-gasified char and/or tars coming from the inlet 168 so as to heat the heat-transfer medium, this heat-transfer medium leaving the combustion means 124 by means of a heat-transfer medium outlet 132 linked to a heat-transfer medium inlet of the gasifier 102 that is, for example, a pipe linking the combustion means 124 and the gasifier 102. This combustion means

124 also comprises an outlet 134 for flue-gases that is, for example, a pipe connected to the combustion means 124.

Using dioxygen as an oxidizer improves the energy yield of the combustion means 124. Using dioxygen allows, in particular, a dramatic reduction in the synthetic gas coming from the gasifier 102 being reused as oxidizer. The surplus dioxygen produced by the electrolysis means 118 can also be recycled in other ways. In addition, the efficiency of the separation chain comprising the condenser 148 and the carbon dioxide separator improves as the dioxygen content in the oxidizer increases.

The composition of the synthetic gas generated by the gasifier 102 changes under the action of the water vapor or of another oxidizing agent, such as for example dioxygen or air, input into the reactor as a result of the thermochemical balances and the production of compounds by heterogeneous gasification of char. For this reason, the synthetic gas produced generally contains pollutants harmful to the lifespan of a catalyst contained in the carbon monoxide methanation means 110. For this reason, a cooling or heat recovery means 150 is placed at the outlet from the gasifier 102 and, at the outlet from this cooling means 150, a separator 138 configured to transmit the separated solids and tars to the combustion means 124. This cooling means 150 is, for example, a heat exchanger. This cooling means 150 enables an exchange of heat to be performed, the heat being recovered to be used elsewhere in the device.

The separator 138 is, for example, a filter configured to retain the solid compounds paired to an absorber to retain the tars. This separator 138 supplies the combustion means 124 with solids thus separated by means, for example, of a pipe. The solids thus retained can be organic compounds, inorganic compounds such as tars, hydrogen sulfide, carbon monoxide sulfide, or a large portion of the water and solids transported with the gas flow. A portion of the gas on output from the separator 138 can be supplied, as necessary, to the combustion means 124.

Similarly, the flue-gas on output from the combustion means 124 is treated in the same way by a cooling or heat recovery means 150 such as, for example, a heat exchanger, cooling the flue-gases, and a gas/solids separator 174 configured to transfer the filtered solids to an outlet 160 for ash and elutriated solids. A portion of the gas, containing dioxygen, on output from this separator 174 can be supplied, as necessary, to the combustion means 124 as oxidizer.

The device comprises a means 110 of methanating the carbon monoxide output from the gasifier 102 that is, for example, a catalytic methanation reactor. This catalytic methanation reactor is, for example, a fixed-bed or fluidized bed reactor, or a reactor/exchanger type. This catalytic methanation reactor transforms the carbon monoxide, dihydrogen and water into carbon dioxide and methane. This carbon monoxide methanation means 110 comprises an inlet 112 for water and for synthetic gas coming from the gasifier 102. This inlet 112 is for example a valve enabling water vapor and synthetic gas to be inserted into the carbon monoxide methanation means 110.

The water vapor enters into the device by means of a first water inlet 152 that supplies the inlet 112 for water and synthetic gas. The addition of water vapor allows the dihydrogen to carbon monoxide ratio to be adjusted close to stoichiometry through the water gas shift reaction ($CO + H_2O = H_2 + CO_2$) and thus to avoid a premature deactivation of the catalyst by coke deposit. The carbon monoxide methanation means 110 produces, on output, methane and carbon dioxide.

The gas mixture on output from the methanation means 110 is cooled by a cooling means 150 that is, for example, a heat exchanger. The output synthetic gas is dehydrated by a condenser 148. This condenser 148 can employ all water reduction techniques or their associations, such as for example heat condensation, adsorption or absorption. The water recovered in this way is transmitted to a water outlet 154. The water output in this way can be evacuated from the device or be supplied to the electrolysis means 118.

The gas mixture on output from the condenser 148 is injected into a carbon dioxide separator 146. The carbon dioxide separator 146 can use all known methods or their combinations, such as, for example, the use of cryogenics, absorption or adsorption. The person skilled in the art will select the solution of his choice provided this solution makes it possible to obtain carbon dioxide with purity above 85% by volume. Too great a volume of carbon monoxide present with the carbon dioxide favors the carbon monoxide methanation reaction at the expense of the carbon dioxide methanation reaction in a methanation reactor 114.

In some variants, the recovered carbon dioxide is treated by an additional purification means configured to remove the carbon monoxide present with the carbon dioxide. In addition to the conventional solutions, such as, for example, adsorption or absorption, the mixture containing the carbon dioxide separated by the separator 146 can undergo thermal oxidation in the combustion means 124. It should be noted that thermal oxidation can only be envisaged if the combustion means 124 operates with pure dioxygen or if the device comprises a carbon dioxide separator on output from the combustion means 124.

In other variants, the device comprises a final carbon monoxide methanation means upstream from the carbon dioxide methanation means 114.

The device comprises a means 114 of methanating the carbon dioxide output from the gasifier 102 that is, for example, a catalytic methanation reactor. This catalytic methanation reactor is, for example, a fixed-bed or fluidized bed reactor, or a reactor/exchanger type. This catalytic methanation reactor transforms the carbon dioxide, dihydrogen and water into carbon dioxide and methane. This carbon dioxide methanation means 114 comprises an inlet 116 for water and for synthetic gas coming from the separator 146. This inlet 116 is for example a valve enabling water vapor and synthetic gas to be inserted into the carbon dioxide methanation means 114. The water vapor enters into the device by means of a first water inlet 166 that supplies the inlet 116 for water and synthetic gas. The carbon dioxide methanation means 114 produces, on output, methane and water.

In addition to the carbon dioxide separated on output from the carbon monoxide methanation means 110, carbon dioxide is recovered from the flue-gases on output from the methanation means 124. To achieve this, the device comprises on output from the gas-solid separator 174 on output from the methanation means 124 a condenser 148 configured to dehydrate the flue-gas output from the separator 174. The water recovered is transferred to a water outlet 162 enabling water to be evacuated from the device or this water to be transferred to the water electrolysis means 118.

On output from this condenser 148, the remaining gas mixture enters a carbon dioxide separator 142 similar to the carbon dioxide separator 146 on output from the carbon monoxide methanation means 110. The gases separated from the carbon dioxide are supplied to an outlet 164 of gases not used by the device. The carbon dioxide separated by the separator 142 is supplied on input to the carbon dioxide methanation means 114.

The methane and water outlet 156 from the carbon dioxide methanation means 114 is connected to the outlet, not shown, from the carbon monoxide methanation means 110, downstream from the cooling means 150.

Downstream from the carbon dioxide separator 146, the device comprises a dihydrogen separator 144. This dihydrogen separator 144 enables the specifications of the synthetic gas to be adjusted to the characteristics of the natural gas. This dihydrogen separator 144 can employ all of the usual methods or a combination of them. The separated dihydrogen is supplied on input to the carbon monoxide methanation means 110 by means of a pipe 156.

The synthetic gas on output from the dihydrogen separator 144 is supplied to a synthetic gas outlet 170 of the device.

The device comprises a water electrolysis means 118 configured to transform the water into dioxygen and dihydrogen. This electrolysis means 118 is, for example, an electrolytic cell comprising two electrodes immersed in the water, each connected to an opposite pole of a source 176 of direct current. This electrolysis means 118 comprises a water inlet 120 that is, for example, a valve enabling water to be injected into the electrolysis means 118. This electrolysis means 118 also comprises a dihydrogen outlet 122 supplying the carbon dioxide methanation means 114. In addition, this electrolysis means 118 comprises a dioxygen outlet 136 supplying an oxidizer inlet 128 of the combustion means 124. Lastly, this device comprises a dioxygen outlet 158 for removing the surplus dioxygen from the device.

Figure 2:
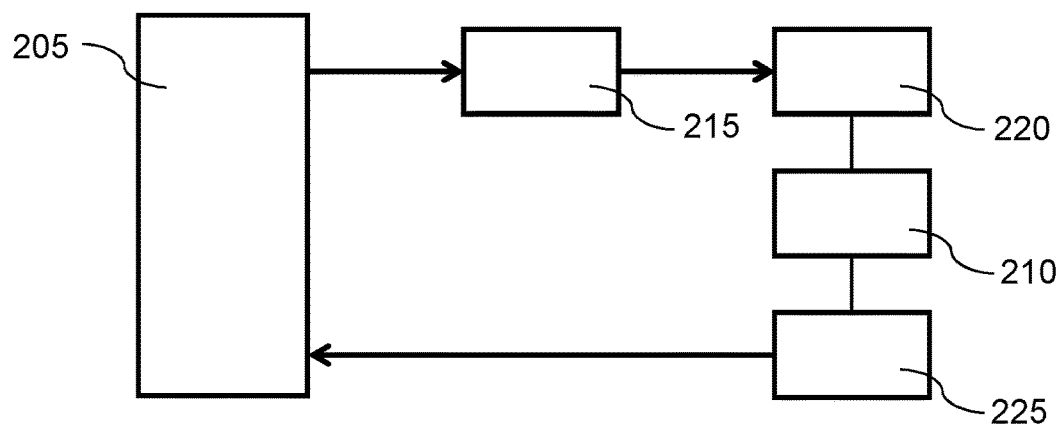
FIG. 2 represents, schematically, a particular embodiment of the network that is the subject of the present invention.

FIG. 2 shows an embodiment of the network that is the subject of the present invention. This network comprises:
- a device 205 for producing substitute natural gas as described in FIG. 1;
- a multi-energy management means 210;
- a pipeline 215 for transporting or distributing gas;
- a means 220 for converting gas into electricity; and
- a generator 225 of direct current.

The multi-energy management means 210 is, for example, a switch that controls:
- the production, by the device 205, and the storage of methane during periods of surplus electricity production; and
- the production of electricity with the stored methane outside these periods.

The periods of surplus electricity production can be predefined in the system or come from an external information source, such as a server for example.

When the multi-energy management means 210 identifies a surplus electricity production period, this management means 210 commands the production of methane. To achieve this, the surplus electricity is used by the direct current generator 225 to supply an electrolysis means, not shown, of the device 205 for producing substitute natural gas. In parallel, biomass and an oxidizing agent is inserted into the gasifier of the device 205 so as to produce synthetic gas. The device 205 produces, on output, substitute natural gas stored by overpressure, above the nominal pressure of the pipelines, in a gas distribution pipeline 215. This overpressure is, for example, of the order of 10%.

When the multi-energy management means 210 identifies a period when the electricity produced is not in surplus, this management means 210 commands the gas-to-electricity conversion means 220 to produce electricity. The gas-to-electricity conversion means 220 is, for example, a gas thermal power plant using the substitute natural gas stored by overpressure in the pipeline 215 to produce electricity.

Figure 3:
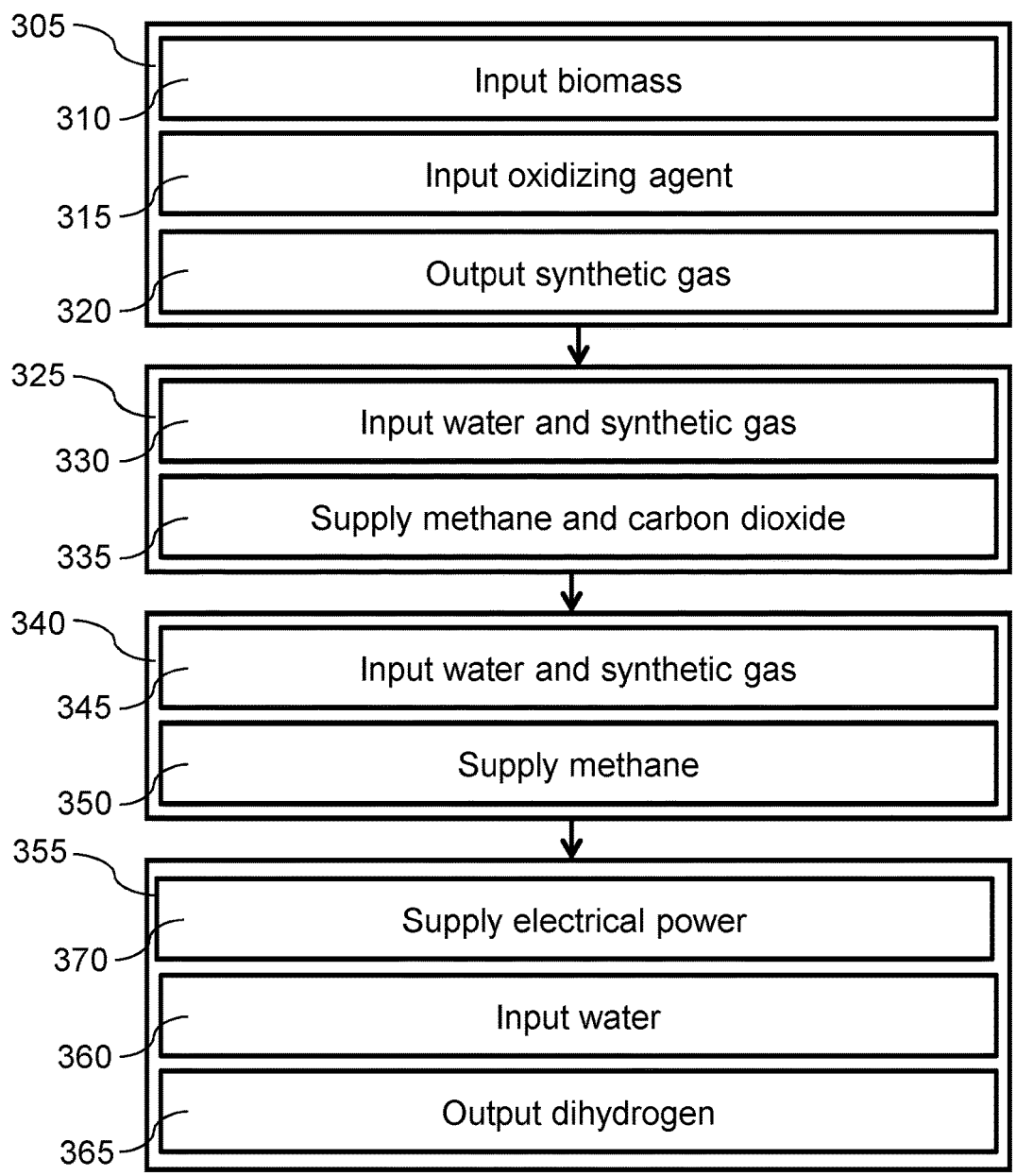
FIG. 3 represents, in the form of a logical diagram, steps in a particular embodiment of the method that is the subject of the present invention.

FIG. 3 shows logical diagram of steps in a particular embodiment of the method that is the subject of the present invention. This method comprises:
- a gasification step 305 to produce a synthetic gas, comprising:
  - a step 310 of inputting biomass;
  - a step 315 of inputting an oxidizing agent; and
  - a step 320 of outputting synthetic gas comprising carbon monoxide;
- a step 325 of methanating the carbon monoxide output from the gasification step 305, comprising a step 330 of inputting water and synthetic gas coming from the gasification step 305, and a step 335 of supplying methane and carbon dioxide;
- a step 340 of methanating the carbon dioxide, comprising a step 345 of inputting water and carbon dioxide coming from the carbon monoxide methanation step 325, and a step 350 of supplying methane;
- a water electrolysis step 355 to transform water into dioxygen and dihydrogen, comprising:
  - a step 370 of supplying electrical power;
  - a step 360 of inputting water, and
  - a step 365 of outputting dihydrogen used during the carbon dioxide methanation step 340.

The gasification step 305 is carried out, for example, by utilizing a gasifier, which is a reactor in which the supplied biomass undergoes a thermochemical conversion to form a synthetic gas ("syngas") containing dihydrogen, carbon monoxide, carbon dioxide, water, tars, or, in general, any type of carbonized compound.

The gasification step 305 comprises a step 310 of inputting biomass, carried out, for example, by utilizing a valve supplying biomass to the gasifier. The gasification step 305 also comprises a step 315 of inputting an oxidizing agent, carried out, for example, by utilizing a valve supplying oxidizing agent to the gasifier. The gasification step 305 further comprises a step 320 of outputting synthetic gas comprising carbon monoxide, carried out, for example, by utilizing a pipe connected to the gasifier.

The method comprises a step 325 of methanating the carbon monoxide output from the gasification step 305, carried out, for example, by utilizing a fluidized bed carbon monoxide methanation means. This carbon monoxide methanation step 325 comprises a step 330 of inputting water and synthetic gas coming from the gasification step 305, carried out, for example, by utilizing a valve of the methanation means. This carbon monoxide methanation step 325 also comprises a step 335 of supplying methane and carbon dioxide+$H_2O$, carried out, for example, by utilizing a pipe on output from the carbon monoxide methanation means.

The method comprises a carbon dioxide methanation step 340, carried out, for example, by utilizing a fluidized bed carbon dioxide methanation means. The carbon dioxide methanation step 340 comprises a step 345 of inputting water and carbon dioxide coming from the carbon monoxide methanation step 325, carried out, for example, by utilizing a water and carbon dioxide insertion valve of the carbon dioxide methanation means. The carbon dioxide methanation step 340 comprises a step 350 of supplying methane, carried out, for example, by utilizing a pipe on output from the carbon dioxide methanation means.

The method comprises a water electrolysis step 355 to transform water into dioxygen and dihydrogen, carried out, for example, by utilizing two electrodes immersed in the water and each connected to an opposite pole of a direct-current generator. The electrolysis step 355 comprises a step 360 of inputting water, carried out, for example, by utilizing a water injection pipe between the two electrodes used during the electrolysis step 355. The electrical supply step 370 is carried out, for example, by connecting the two electrodes to a source of direct current. The electrolysis step 355 comprises a step 365 of outputting dihydrogen used during the carbon dioxide methanation step 340, carried out, for example, by utilizing a pipe.

In some variants, the method 30 also comprises a combustion step, comprising:
- a step of inputting a solid portion resulting from pyrolysis of a non-gasified solid combustible, also called "char", coming from the gasifier and transported by a heat transfer medium;
- an oxidizer input step;
- a non-gasified char combustion step for heating the heat transfer medium;
- a heat transfer medium output step linked to an input of heat transfer medium for the gasifier; and
- a step of outputting flue-gases.

In some variants, the dihydrogen production step carries out water electrolysis comprising a step of outputting dioxygen supplying the oxidizer inlet of a combustion means utilized during the combustion step.

In some variants, the method 30 comprises, between the step of outputting gaseous compound from the gasifier and the step of inputting gaseous compound of the carbon monoxide methanation step, a step of separating the gases from the solids and/or tars in the gaseous compound, and a step of transmitting the separated solids and/or tars to the combustion means utilized during the combustion step.

In some variants, the method 30 comprises a step of recycling a portion of the flue-gas, on output from the combustion step, comprising dioxygen, towards an oxidizer inlet of the combustion means utilized during the combustion step.

In some variants, the method 30 comprises, downstream from the flue-gas output step of the combustion step, a carbon dioxide separation step to supply the carbon dioxide methanation means, utilized by the carbon dioxide methanation step, with carbon dioxide.

In some variants, the method 30 comprises a dihydrogen separation step, downstream from the carbon monoxide methanation step, to supply the carbon monoxide methanation means, utilized during the carbon monoxide methanation step, with dihydrogen.

In some variants, the method 30 comprises, downstream from the carbon monoxide methanation step, a carbon dioxide separation step to supply the carbon dioxide methanation means, utilized during the carbon dioxide methanation step.

In some variants, an output step of the carbon dioxide methanation step is linked to an output step of the carbon monoxide methanation step.

In some variants, the method 30 comprises, downstream from the carbon monoxide methanation step and/or from the combustion step, a step of condensing the water contained in vapors and supplying the electrolysis step with water.

The invention claimed is:

1. Integrated device for producing a substitute natural gas, comprising:
   a gasifier configured to produce a gaseous compound from a biomass, comprising:
   an inlet for the biomass;
   an inlet for an oxidizing agent; and
   an outlet for the gaseous compound comprising carbon monoxide;
   first and second methanation units arranged in series and configured to produce a mixture of substitute natural gas and dihydrogen from the gaseous compound, wherein the first methanation unit is a carbon monoxide methanation unit configured to methanate the carbon monoxide and produce the mixture of substitute natural gas and dihydrogen together with carbon dioxide; and wherein the first methanation unit having at least one inlet for water and an inlet for the gaseous compound, and wherein the second methanation unit is a carbon dioxide methanation unit configured to methanate the carbon dioxide from the first methanation unit and to produce the mixture of substitute natural gas and dihydrogen; and wherein the second methanation unit having at least one inlet for dihydrogen and an inlet for the carbon dioxide;
   a dihydrogen separator configured to separate dihydrogen from the mixture of substitute natural gas and dihydrogen and to supply the first methanation unit with dihydrogen; and
   an electrolysis unit to produce dihydrogen from the water and an electric current, comprising:
   an electrical power supply;
   an inlet for the water; and
   an outlet for supplying dihydrogen to the second methanation unit.

2. The Integrated device according to claim 1, further comprising a combustion unit, comprising:
   an inlet for a solid portion resulting from a pyrolysis of a non-gasified solid combustible from the gasifier and transported by a heat transfer medium;
   an oxidizer inlet;
   a non-gasified char combustor to heat the heat transfer medium;
   a heat transfer medium outlet linked to a heat transfer medium inlet of the gasifier and
   an outlet for a flue-gas.

3. The integrated device according to claim 2, wherein the electrolysis unit is configured to carry out an electrolysis of the water, and comprises a dioxygen outlet to supply the oxidizer inlet of the combustion unit.

4. The integrated device according to claim 2, further comprising a separator between the gaseous compound outlet of the gasifier and the gaseous compound inlet of the carbon monoxide methanation unit, the separator is configured to separate at least one of gases from solids and tars in the gaseous compound, and the separator is configured to transmit at least one of separated solids and the tars to the combustion unit.

5. The integrated device according to claim 2, further comprising a recycling unit to recycle a portion of the flue-gas output from the combustion unit towards an oxidizer inlet of the combustion unit, wherein the flue-gas comprises dioxygen.

6. The integrated device according to claim 2, further comprising a carbon dioxide separator downstream from the flue-gas outlet of the combustion unit, the carbon dioxide separator is configured to supply the carbon dioxide methanation unit with the carbon dioxide.

7. The integrated device according to claim 1, further comprising a carbon dioxide separator downstream from the carbon monoxide methanation unit, the carbon dioxide separator is configured to supply the carbon dioxide methanation unit with the carbon dioxide.

8. The integrated device according to claim 1, wherein an outlet from the carbon dioxide methanation unit is linked to an outlet from the carbon monoxide methanation unit.

9. The integrated device according to claim 2, further comprising a condenser downstream from at least one of the carbon monoxide methanation unit and the combustion unit, the condenser is configured to condense the water contained in vapors and to supply the electrolysis unit with the water.

10. A network comprising at least one integrated device for producing substitute natural gas, said at least one integrated device comprising:
  a gasifier configured to produce a gaseous compound from a biomass, comprising:
  an inlet for biomass;
  an inlet for an oxidizing agent; and
  an outlet for the gaseous compound comprising carbon monoxide;
  first and second methanation units arranged in series and configured to produce a mixture of substitute natural gas and dihydrogen from the gaseous compound, wherein the first methanation unit is a carbon monoxide methanation unit configured to methanate the carbon monoxide and produce, the mixture of substitute natural gas and dihydrogen together with carbon dioxide; and wherein the first methanation unit having at least one inlet for water and an inlet for the gaseous compound; and wherein the second methanation unit is a carbon dioxide methanation unit configured to methanate the carbon dioxide from the first methanation unit and to produce the mixture of substitute natural gas and dihydrogen; and wherein the second methanation unit having at least one inlet for for dihydrogen and an inlet for the carbon dioxide;
  a dihydrogen separator configured to separate dihydrogen from the mixture of substitute natural gas and dihydrogen and to supply the first methanation unit with dihydrogen; and
  an electrolysis unit to produce dihydrogen from water and electric current, comprising:
  an electrical power supply;
  an inlet for water; and
  an outlet for supplying dihydrogen to the second methanation unit.

11. The network according to claim 10, further comprising a multi-energy management unit to control:
  production, with said at least one integrated device, and storage of methane during periods of surplus electricity production; and
  production of electricity with the stored methane outside the periods of surplus electricity production.

12. The network according to claim 11, further comprising gas distribution pipelines, the storage of methane to generate the electricity is realized by overpressure above a nominal pressure of the gas distribution pipelines.

13. Method for producing a substitute natural gas, comprising:
  producing a gaseous compound from a biomass, comprising the steps of:
  inputting the biomass;
  inputting an oxidizing agent; and
  outputting the gaseous compound comprising carbon monoxide from a gasifier;
  methanating, in a first methanation unit and a second methanation unit arranged in series, the gaseous compound to produce a mixture of substitute natural gas and dihydrogen, wherein the first methanation unit is a carbon monoxide methanation unit configured to methanate the carbon monoxide and produce the mixture of substitute natural gas and dihydrogen together with carbon dioxide; and wherein the first methanation unit having at least one inlet for water and an inlet for the gaseous compound; and wherein the second methanation unit is a carbon dioxide methanation unit configured to methanate the carbon dioxide from the first methanation unit and to produce the mixture of substitute natural gas and dihydrogen; and wherein the second methanation unit having at least one inlet for dihydrogen and an inlet for the carbon dioxide coming from first methanation unit produce a mixture of substitute natural gas and dihydrogen together with carbon dioxide;
  separating with a dihydrogen separator the dihydrogen from the mixture of substitute natural gas and dihydrogen and supplying the first methanation unit with said dihydrogen; and,
  producing dihydrogen from the water and an electric current, comprising the steps of:
  supplying an electrical power;
  inputting the water; and
  outputting dihydrogen and supplying same to said second methanation unit.

14. The method according to claim 13, further comprising the step of combustion, comprising the steps:
  inputting a solid portion resulting from a pyrolysis of a non-gasified solid combustible from the gasifier and transported by a heat transfer medium;
  inputting an oxidizer;
  heating the heat transfer medium by a non-gasified char combustion;
  linking an output of the heat transfer medium to an input of the gasifier for the heat transfer medium; and
  outputting a flue-gas.

15. The method according to claim 14, wherein the step of producing dihydrogen comprises a water electrolysis comprising the step of outputting dioxygen to supply an oxidizer inlet of a combustion unit utilized during the step of combustion.

16. The method according to claim 14, between the steps of outputting gaseous compound from the gasifier and inputting the gaseous compound of the carbon monoxide methanation step, further comprising the steps of separating the gases from at least one of solids and tars in the gaseous compound, and transmitting at least one of the separated solids and tars to a combustion unit utilized during the combustion step.

17. The method according to claim 14, further comprising the step of recycling a portion of the flue-gas output from the combustion step towards an oxidizer inlet of a combustion unit utilized during the combustion step, the flue gas comprises dioxygen.

18. The method according to claim 14, further comprising the step of separating the carbon dioxide from the flue-gas output during the combustion step to supply the carbon dioxide to a carbon dioxide methanation unit utilized by the carbon dioxide methanation step.

19. The method according to claim 13, further comprising the step of separating the carbon dioxide from an output of the carbon monoxide methanation step to supply a carbon dioxide methanation unit, utilized during the carbon dioxide methanation step.

20. The method according to claim 13, further comprising the step of linking an output of the carbon dioxide methanation step to an output of the carbon monoxide methanation step.

21. The method according to claim 13, that comprises, downstream from the carbon monoxide methanation step and/or from the combustion step, a step of condensing the water contained in vapors and supplying the electrolysis step with water.

\* \* \* \* \*